United States Patent

Kuhl

[11] Patent Number: 5,898,488
[45] Date of Patent: Apr. 27, 1999

[54] METHOD AND APPARATUS FOR CANDLING EGGS AND FILLING TRAYS WITH FERTILE EGGS

[76] Inventor: Jeffrey B. Kuhl, 61 Kuhl Rd., Flemington, N.J. 08822

[21] Appl. No.: 08/784,666

[22] Filed: Jan. 21, 1997

[51] Int. Cl.⁶ .......................... G01N 33/08; A01K 43/00
[52] U.S. Cl. .................. 356/53; 356/55; 356/58
[58] Field of Search ................... 356/52, 53, 55, 356/58, 54, 56–57, 59–61

[56] References Cited

U.S. PATENT DOCUMENTS

| | | | |
|---|---|---|---|
| 2,497,655 | 2/1950 | Bramson | 356/56 |
| 2,708,515 | 5/1955 | Bliss . | |
| 2,823,800 | 2/1958 | Bliss . | |
| 2,987,182 | 6/1961 | Ator et al. . | |
| 3,031,077 | 4/1962 | Mumma et al. . | |
| 3,077,257 | 2/1963 | Niederer et al. | 356/56 |
| 3,232,413 | 2/1966 | Niederer et al. . | |
| 3,255,660 | 6/1966 | Hirt . | |
| 3,492,073 | 1/1970 | Michael . | |
| 3,540,824 | 11/1970 | Fonda et al. . | |
| 3,740,144 | 6/1973 | Walker . | |
| 4,039,259 | 8/1977 | Saito et al. . | |
| 4,063,822 | 12/1977 | deJong et al. . | |
| 4,268,168 | 5/1981 | Dewaele . | |
| 4,519,505 | 5/1985 | Thomas . | |
| 4,671,652 | 6/1987 | van Asselt et al. . | |
| 4,937,619 | 6/1990 | Fukuda et al. . | |
| 4,978,225 | 12/1990 | Reimer . | |
| 5,017,003 | 5/1991 | Keromnes et al. . | |
| 5,030,001 | 7/1991 | vande Vis . | |
| 5,173,737 | 12/1992 | Mitchell et al. . | |
| 5,504,572 | 4/1996 | Taylor et al. . | |

Primary Examiner—Frank G. Font
Assistant Examiner—Amanda Merlino
Attorney, Agent, or Firm—Sperry, Zoda & Kane

[57] ABSTRACT

The apparatus of the present invention provides a means for candling eggs and providing trays of eggs filled with candled eggs and includes a provision wherein infertile eggs are removed from trays of fertile eggs and are replaced with fertile eggs in order to supply a complete array of fertile eggs within the tray. The apparatus includes a conveying means removing trays of eggs from an infeed station to an outfeed station. The trays of eggs supplied at the outfeed station preferably are completely filled with fertile eggs only and usually will be supplied to a processing station such as for inoculation. The apparatus includes four stations with candling performed at the first station by a video camera with infertile eggs moved to an exit hopper at a second station thereadjacent. Initially fertile eggs are also transferred to the second station where they are placed into a buffer tray which is then moved to the third station and provides a source of fertile eggs for replacing of removed infertile eggs from future candled trays. Once the buffer contains eggs a tray will pass in the infeed through the first station, will be candled, and the infertile eggs will be removed and the conveyor will then move this tray of all fertile eggs with a few open egg receiving recesses to the fourth station.

40 Claims, 5 Drawing Sheets

METHOD AND APPARATUS FOR CANDLING EGGS AND FILLING TRAYS WITH FERTILE EGGS

BACKGROUND OF THE INVENTION

1. Field of the Invention

The present invention deals with the field of devices utilized for candling eggs. Candling eggs has been performed for many years in order to accurate determine that an egg includes a valuable embryo such that it will ultimately yield a chick. The best manner of making this determination is to pass light through an egg. If the egg is opaque the egg contains an embryo. However, if the egg is clear this is an indication that no embryo has developed and the egg can be otherwise processed or discarded.

Such candling operations have been done manually for many years, however, automated candling systems have recently been developed. Normally it is necessary during manually candling for the candling operator to be positioned above the eggs traveling upon a conveyor with a light below the conveyor passing upwardly through the eggs. With this configuration the observing candler operator is normally located within a dark enclosure above the conveyor to enhance accuracy in candling. Recently automated systems have been developed for candling, however, none disclose the method and apparatus of the present invention which utilizes the analysis of the digital video camera image recorded during candling to allow removal of infertile eggs with a subsequent downstream re-introduction of fertile eggs into the openings provided when the infertile eggs are moved.

2. Description of the Prior Art

In the current state-of-the-art the speed of candling is one of the most important considerations necessary and incident to a candling system. Many automated systems use high speed egg movement with multiple observers attempting to remove as many of the clear or infertile eggs which they can locate. Some at tempts have been made to use still photographs for analyzing whether an egg is fertile or infertile. Such systems have proved inadequate especially in view of the high speed egg processing machinery available today.

It is also imperative that the trays of eggs be completely filled with fertile eggs and that no infertile eggs be included therein. This is true because all such eggs are normally fed to an inoculation station where they are inoculated against disease normally within two and four weeks after being dropped and gathered. The inoculation medium and the inoculation step both require time and significant expense and for this reason it is best that eggs being transferred to this inoculation stage be arranged in fully filled rows of fertile only eggs. The present invention provides a means for achieving this desired result not possible heretofore as prior art.

SUMMARY OF THE INVENTION

The present invention provides a method as well as an apparatus designed for candling eggs and for filling trays completely with an array of fertile eggs. Each tray preferably defines an array of egg receiving tray recesses each of which should be filled with a fertile egg.

The apparatus includes a main conveyor designed to move egg trays as desired from an infeed station where trays of eggs are received and an outfeed station where completely filled trays of fertile eggs preferably exit. The outfeed station is positioned downstream from the infeed station and they are longitudinally spaced from one another. A controller is also included operatively connected to the main conveying means in order to selectively control operation thereof and move the egg trays therealong from the infeed station to the outfeed station. The controller preferably includes a video frame grabber to facilitate candling.

The apparatus includes a first station positioned adjacent the main conveying apparatus for candling trays of eggs transferred thereon from the infeed station responsive to operation of the main conveyor. The first station preferably includes a primary lighting apparatus positioned below the main conveying apparatus which is adapted to transmit light upwardly therefrom through each egg located upon a tray on the main conveyor. In this manner candling will be greatly facilitated. Each egg tray and main conveyor is preferably at least partially translucent and/or even could be transparent in such a manner as to allow light from the primary lighting means to pass therethrough to eggs positioned upon the egg receiving tray recesses. The primary lighting apparatus preferably includes a plurality of individual lighting modules therein operatively connected to the control means to facilitate accurate controlling of the lighting therewith by providing fine resolution to the ultimate lighting by separate control of the individual lighting modules.

A candling camera may be included which preferably comprises a digital video camera positioned above the main conveyor and directed downwardly in such a manner as to provide photographically recorded video tape images of any trays of eggs traveling within the first station on the main conveyor therebelow during candling. The candling camera preferably is operatively secured to the controller in such a manner as to communication these recorded images thereto for analysis. A camera housing may also be included positioned extending about the candling camera in order to enhance the images recorded therewith to further facilitate egg candling.

A second station may be included location laterally adjacent to the first station. This second station preferably includes a transfer head movably mounted to the second station. The transfer head is preferably movable between a first transfer head position within the first station and a second transfer head position within the second station. The transfer head preferably includes a plurality of egg gripping members such as vacuum gripping cups extendable downwardly therefrom and adapted to grasp an egg therebelow while located within the first transfer head position to facilitate lifting and removal of eggs selectively from egg trays in the first station for movement therealong with the transfer head to the second transfer head position in the second station. Gripping of the eggs is preferably achieved by applying of a vacuum to these vacuum gripping cups.

The transfer head preferably is also operatively connected to the controller to control movement thereof between the first transfer head position and the second transfer head position and gripping of eggs by the egg gripping means. This first transfer head position of the first transfer head is preferably located within the first station below the candling camera and above the main conveyor therein and above any tray of eggs therein also.

An exit hopper may also be included positioned below the second transfer head position within the second station. This exit hopper is preferably adapted to receive and accumulate infertile eggs released from the egg gripping cups of the transfer head while in the second transfer head position within the second station. The transfer head is preferably also operable responsive to the control means determining the presence of at least one infertile egg within an egg tray in the first station to move to the first transfer head position above the egg tray and actuate the vacuum of those cups in abutment with any infertile egg in order to remove them from the egg tray for movement to the second transfer head position for release into the exit hopper.

The controller is also operative to indicate an infertile egg responsive to an egg within the egg tray in the first station whenever an egg has a translucence greater than the average egg sensed within the egg tray plus a predetermined threshold value resulting in movement thereof by the transfer to the exit hopper. The exit hopper normally actually comprises a disposable receptacle for disposing of the infertile eggs. In some situation they are utilized for livestock feed or fertilizer, however, normally they are discarded.

A third station is also included positioned longitudinally adjacent the second station and adjacent the main conveyor. This third station preferably includes a buffer tray movably positioned therein. The buffer tray preferably defines a plurality of egg receiving buffer recesses therein for holding of fertile eggs to facilitate placement onto egg trays upon the main conveyor prior to movement thereof to the outfeed station. This buffer tray preferably is movable between a buffer rest position within the third station ready to supply fertile eggs and a buffer receiving position within the second station ready to be charged or loaded with fertile eggs. The buffer tray is also operatively connected to the control means to control movement thereof between the buffer rest position and the buffer receiving position needed selectively. Also the transfer head is operable responsive to the control means determining that the buffer tray is empty of fertile eggs to move to the first transfer head position above the egg tray and to actuate the egg gripping means in abutment with all eggs located within the egg tray therebelow and to carry them to the second transfer head position.

The control means is also responsive to cause deactivation of any of those egg gripping members or cups holding an infertile egg thereon for movement into the exit hopper therebelow. The buffer tray is preferably operable responsive to the controller determining that the buffer tray is empty of fertile eggs to move to the buffer receiving position within the second station below the transfer head and responsive to the control means deactivating the egg gripping members thereof to allow placement of fertile eggs therefrom into the egg receiving buffer recesses for reloading the buffer tray.

The controller is also operative responsive to the buffer tray being reloaded with fertile eggs to move to the buffer rest position within the third station in order to supply fertile eggs into empty egg receiving tray recesses within egg trays located in the fourth station.

A buffer camera is included located above the buffer rest position of the buffer tray and is directed downwardly in order to provide photographically recorded images of the positions of fertile eggs located within the buffer tray therebelow. The buffer camera preferably is operatively connected to the controller to provide recorded images thereto of positions of fertile eggs within the buffer tray.

A fourth station is included positioned longitudinally along the main conveying means downstream of the first station adjacent the outfeed station and laterally adjacent the third station. The fourth station is adapted to receive egg trays moved to the main conveyor from the first station.

An empty tray removal apparatus is also preferably included positioned adjacent the fourth station and is operative to remove any empty egg trays therefrom prior to movement thereof to the outfeed station.

A verification camera is also preferably included positioned above the main conveying means and is directed downwardly to be operative to determine whether an egg tray positioned upon the main conveyor within the fourth station is empty in order to initiate operation of the empty tray removal to prevent any empty tray from moving to the outfeed station.

A pick and place device is also included in the present invention which is normally positioned adjacent to the third and fourth stations and is operatively secured to the controller. The controller is operative responsive to any of the egg receiving tray recesses being empty as indicated by the analysis of the recorded photograph image from the candling camera to urge the pick and place device to move to the third station above the buffer tray for selective removal of at least one or more fertile eggs therefrom. These fertile eggs will thereafter be moved by the pick and place device to the fourth station above the egg tray on the main conveyor therein in order to place the fertile egg into each of the empty egg receiving recesses defined in the tray currently located within the fourth station. The pick and place device preferably has fully controlled movement in three dimensional directions including vertically, laterally, as well as longitudinally. In this manner the pick and place device will facilitate the movement of fertile eggs from the egg receiving buffer recesses within the third station into the egg receiving tray recesses of the egg trays located in the fourth station.

It is an object of the present invention to provide a method and apparatus for candling eggs and filling trays with fertile eggs wherein high intensity light is passed through an array of eggs in a tray to determine whether the eggs are fertile or infertile.

It is an object of the present invention to provide a method and apparatus for candling eggs and filling trays with fertile eggs wherein infertile eggs are automatically removed from trays of eggs and replaced with fertile eggs such that all the egg receiving recesses within a given tray are filled with fertile eggs only.

It is an object of the present invention to provide a method and apparatus for candling eggs and filling trays with fertile eggs wherein the cost for the application of inoculation vaccine is minimized.

It is an object of the present invention to provide a method and apparatus for candling eggs and filling trays with fertile eggs wherein the processing time and cost for vaccinating eggs is minimized.

It is an object of the present invention to provide a method and apparatus for candling eggs and filling trays with fertile eggs wherein use with any type of a processing station designed to receive fertile eggs is made possible.

It is an object of the present invention to provide a method and apparatus for candling eggs and filling trays with fertile eggs wherein manual labor costs are significantly reduced.

It is an object of the present invention to provide a method and apparatus for candling eggs and filling trays with fertile eggs wherein the initial capital cost outlay for equipment is minimized.

It is an object of the present invention to provide a method and apparatus for candling eggs and filling trays with fertile eggs wherein the number of moving parts is minimized.

It is an object of the present invention to provide a method and apparatus for candling eggs and filling trays with fertile eggs wherein maintenance costs are minimized.

It is an object of the present invention to provide a method and apparatus for candling eggs and filling trays with fertile eggs wherein a minimum amount of floor space is required.

It is an object of the present invention to provide a method and apparatus for candling eggs and filling trays with fertile eggs wherein use with conventionally available video technology is available.

It is an object of the present invention to provide a method and apparatus for candling eggs and filling trays with fertile eggs wherein increased reliability of candling is achieved.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
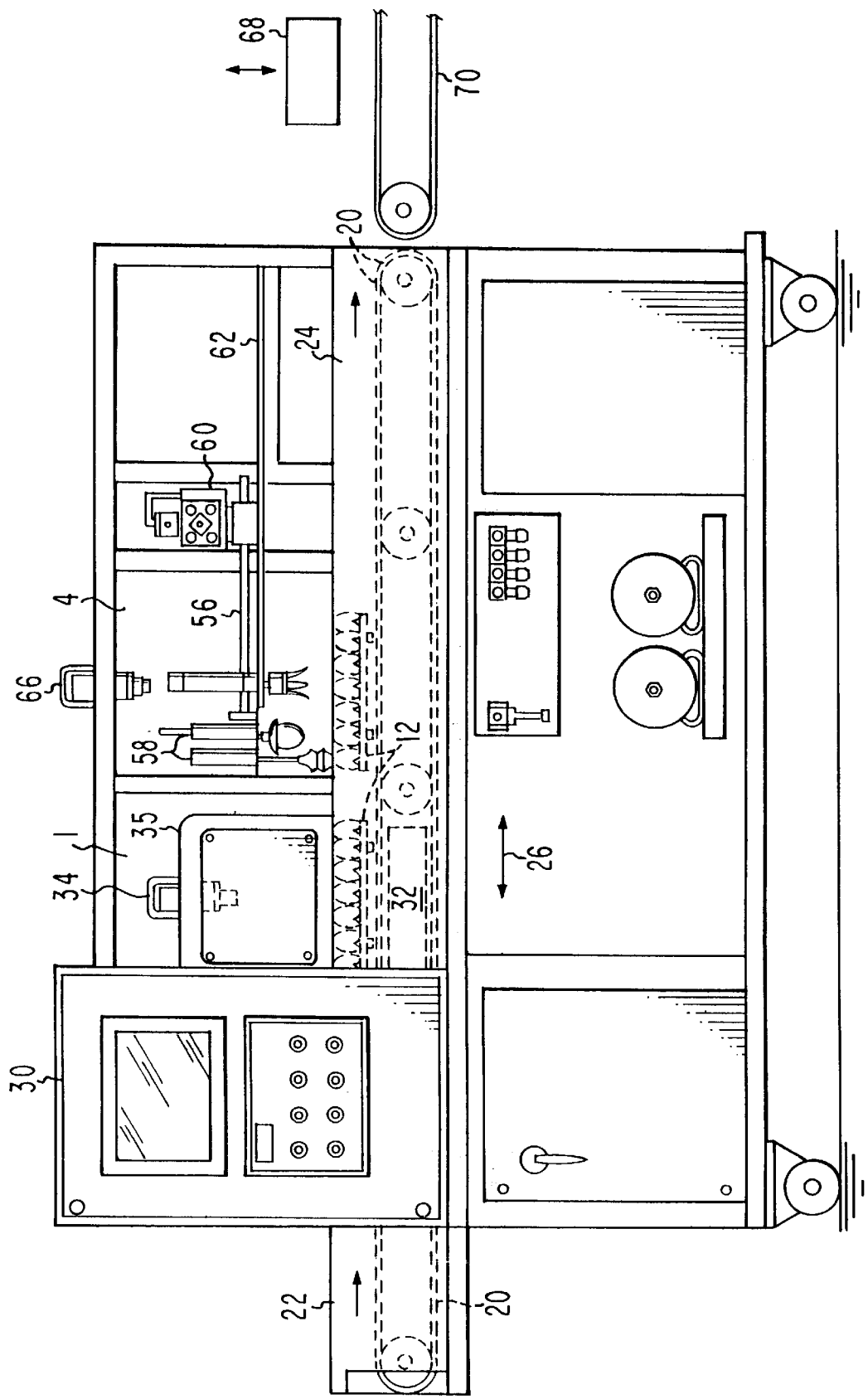
FIG. 1 is a side plan view of an embodiment of the apparatus for candling eggs and filling trays having an array of egg receiving recesses therein.
Figure 2:
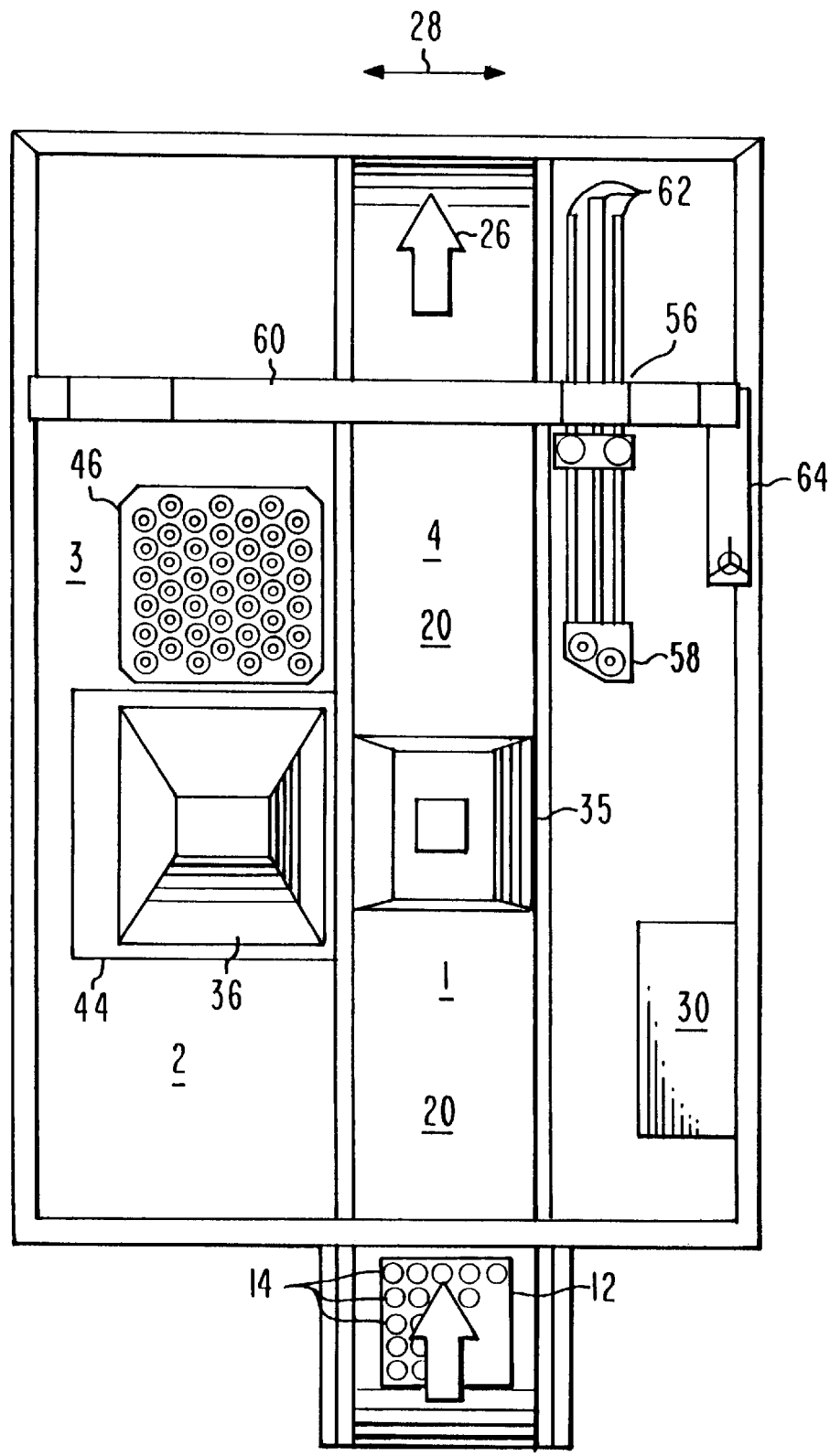
FIG. 2 is a top plan view of the embodiment shown in FIG. 1.
Figure 3:
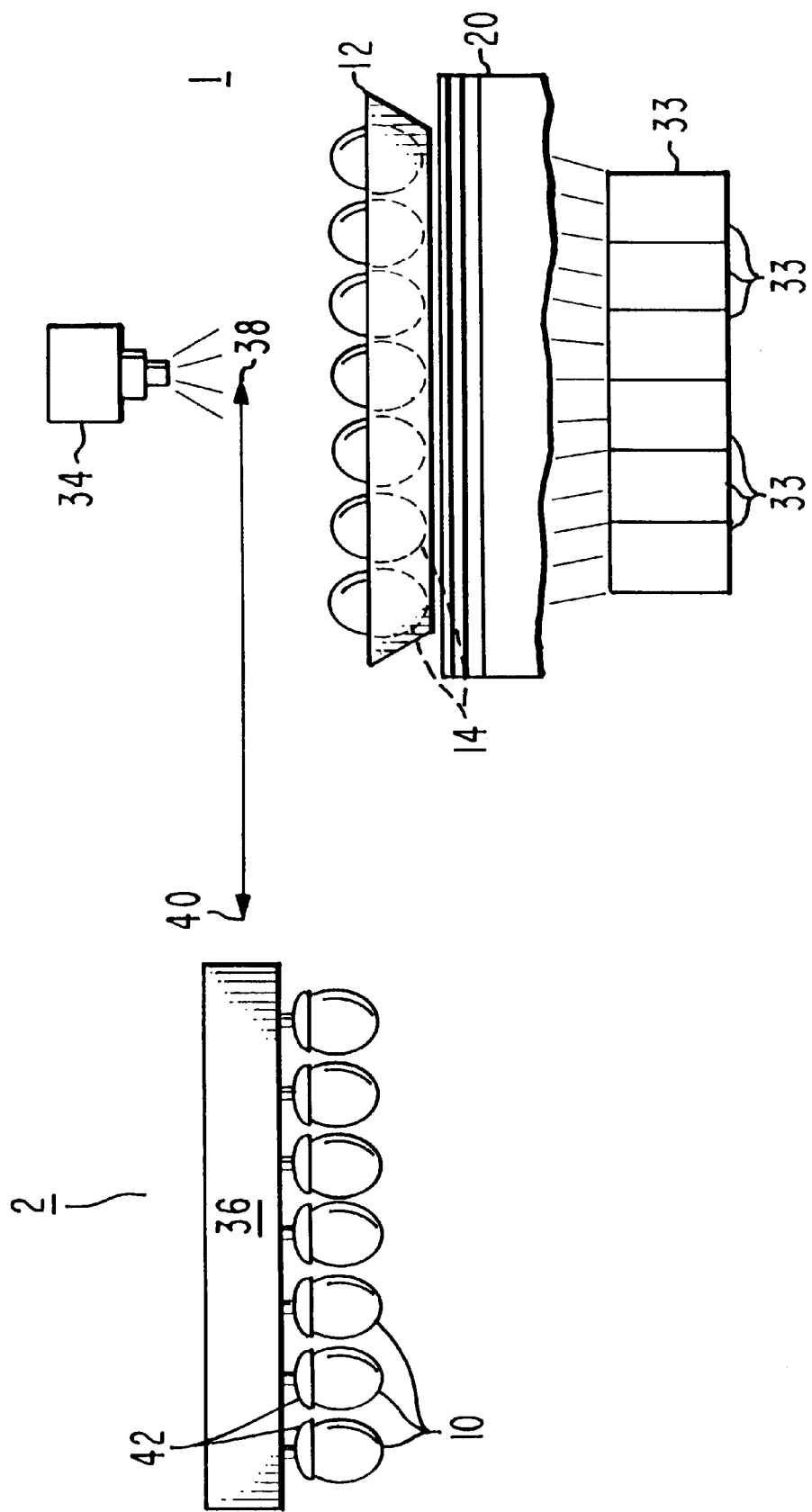
FIG. 3 is a side schematic illustration of an embodiment of stations 1 and 2 of the present invention.
Figure 4:
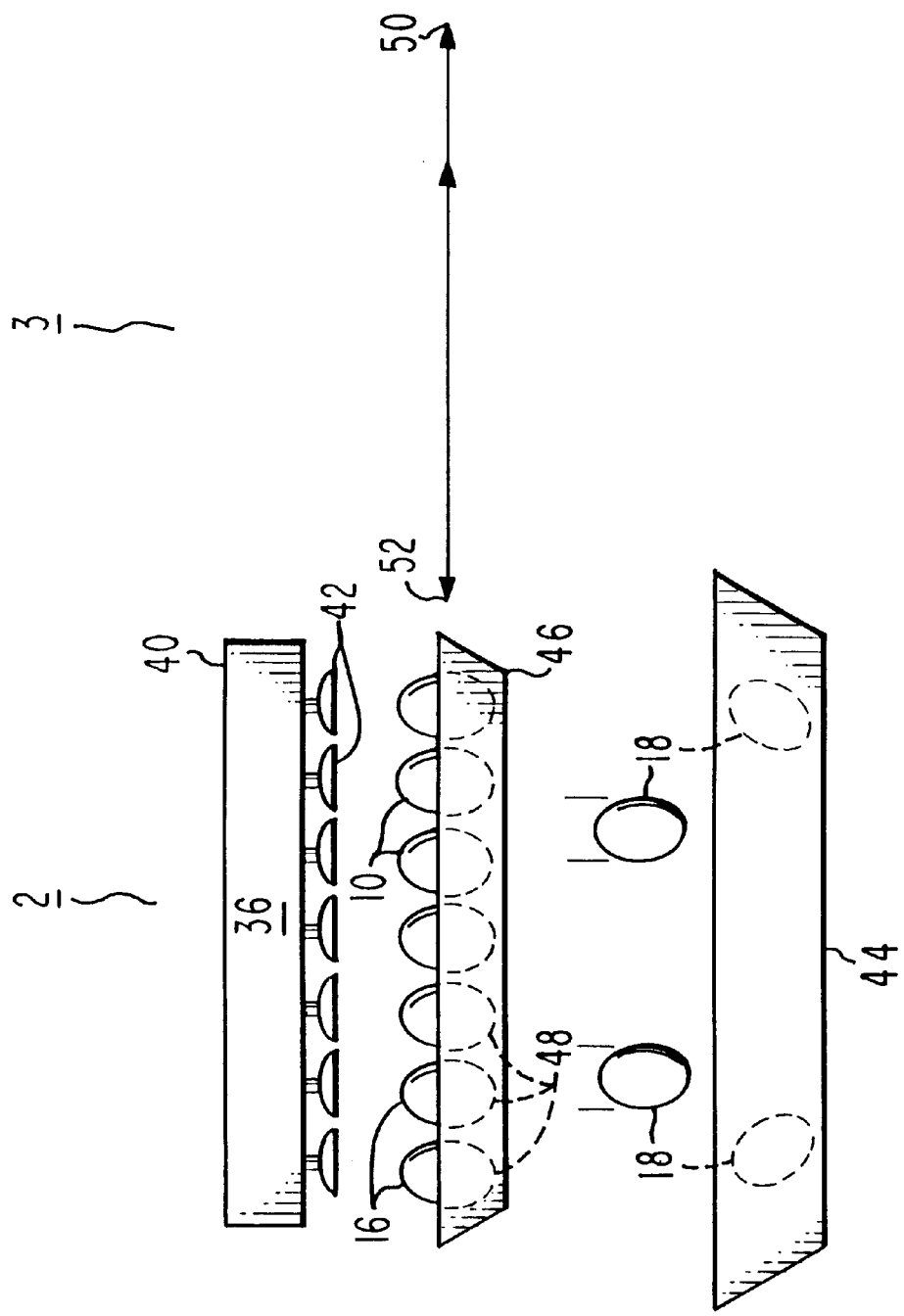
FIG. 4 is a side schematic illustration of an embodiment of stations 2 and 3 of the present invention.
Figure 5:
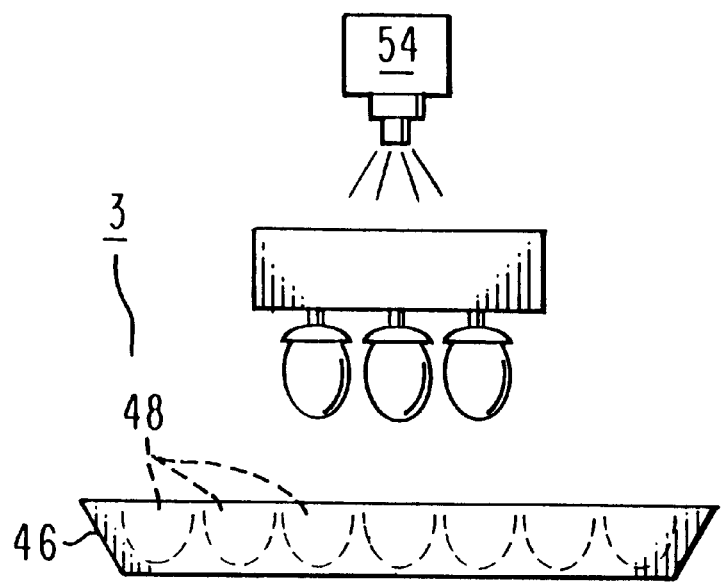
FIG. 5 is a side schematic illustration of an embodiment of station 3 of the present invention.
Figure 6:
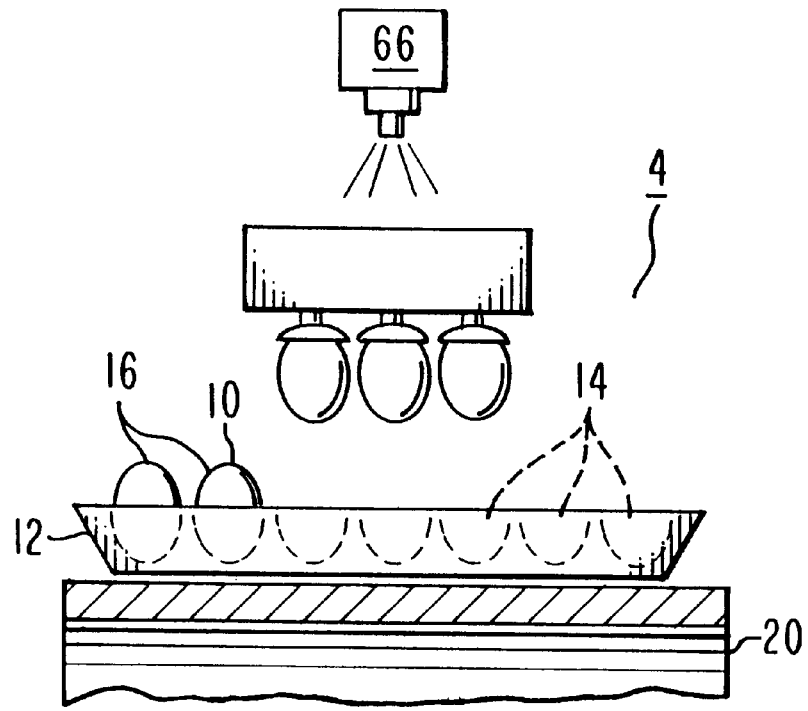
FIG. 6 is a side schematic illustration of an embodiment of station 4 of the present invention.

The present invention provides a device which is particularly usable for the candling of eggs and for filling egg trays 12 with eggs 10 such that all of the egg receiving recesses 14 thereof are filled with fertile eggs 16. With this apparatus the infertile eggs 18 are removed and accumulated and possibly discarded and the egg receiving recesses 14 from which these infertile eggs 18 were withdrawn are filled with fertile eggs 16. To practice this method the apparatus of the present invention includes a main conveying member 20 which preferably runs in one direction from an infeed station 22 where trays of eggs are received to an outfeed station 24 where trays of fertile eggs are provided for processing such as vaccination against diseases. For the purposes of the present application, the longitudinal direction 26 shall be taken as the direction of movement of the main conveyor 20 from the infeed station 22 to the outfeed station 24. The lateral direction is shown by arrow 28.

With the apparatus of the present invention a control member 30 will be defined to control the operation of various components located at the four operative stations of the present invention. These operative stations are defined as first station 1, the second station 2, the third station 3 and the fourth station 4.

In a tray 12 of eggs 10 in this first position of the infeed station 22 the main conveyor 20 will carry it to the first station 1. First station 1 includes a primary lighting means 32 preferably located below the main conveyor 20. The primary lighting fixture is designed to transmit light upwardly through the preferably translucent or open conveyor 20 and through the translucent or open egg trays 12 such that the light passes upwardly through eggs 10 for candling. Observation for candling is performed by a candling camera positioned above the main conveyor which is directed downwardly to provide a photographically recorded image of the eggs within a tray positioned upon the first station 1. Normally during candling the main conveyor 20 will not be running and, as such, the tray 12 of eggs 10 will be stationary within the first station 1.

Preferably the candling camera 34 will comprise a digital video camera which will be capable of rendering a digitized video image for analysis by the control means 30. With a video frame grabber included within the apparatus of the controller 30 the analysis of these digitized individual video frames will be significantly enhanced. Also to further enhance operation of the candling camera 34 a camera housing 35 preferably extends about the digital video camera 34. This camera housing will place the digital video camera 34 itself in a dark environment but will have an open bottom area to allow the camera to clearly view trays 12 of eggs 10 located therebelow.

Further control of candling is achieved by dividing the primary light 32 into individual lighting modules 33. These individual lighting modules 33 can actually be so finely controlled as to comprise a single bulb for each egg 10 traveling upon an array. Normally the array of eggs 10 will be seven columns of six rows each for a total of forty-two eggs within a tray and forty-two individual bulbs could be separately controlled or the bulbs could be grouped into modules of more than one bulb which themselves could be individually controlled. In either case the individual light modules 33 provide a significant ability to refine the lighting conditions for candling other than merely turning the primary light means 32 on or off by having some of the individual light modules 33 on and others off more accurate control of lighting is achieved depending upon the ambient conditions and the candling environment generally.

The present invention further includes a second station 2 located laterally adjacent to the first station 1. This second station 2 preferably includes a transfer head 36 movably mounted therewithin. The transfer head 36 is movable between a second transfer head position 40 defined within the second station 2 and a first transfer head position 38 within the first station 1. The transfer head 36 preferably also includes a plurality of egg gripping devices such as vacuum gripping cups 42 which extend downwardly therefrom and are adapted to grasp an egg therebelow within abutment therewith. In this manner lifting or removal of eggs 10 selectively from egg trays 12 located within the first station 1 is achieved. Such removed eggs 10 will be capable of movement with the transfer head 36 from the first transfer head position 38 to the second transfer head position 40. The transfer head 36 will then be operable to release infertile eggs 18 from movement into the exit hopper 44 located therebelow. The transfer head 36 will also be operatively connected to the control device to control movement there of between the first and second transfer head positions 38 and 40. The exit hopper 44 will be positioned below the second transfer head position 40 of transfer head 36 and will be adapted to receive and accumulate infertile eggs 18 released from the egg gripping cups 42 of the transfer head 36.

The third station 3 will include a buffer container or tray 46 movable therein. This third station 3 will be positioned longitudinally adjacent to the second station 2 and adjacent to the main conveyor 20. The buffer container 46 of the third station 3 will define a plurality of egg receiving buffer recesses 48 therein for the holding of fertile eggs 16. These eggs are made available for movement into the open egg receiving recesses 14 of trays 12 after infertile eggs 18 are removed therefrom by the transfer head 36. The buffer container 46 provides a supply of fertile eggs 18 for this replacement.

The buffer container 46 is movable between a buffer rest position 50 within the third station 3 ready to provide fertile eggs therefrom and a buffer receiving position 52 within the second station 2. The buffer receiving position 52 is located within the second station 2 below the first transfer head position 38 of the transfer head 36 and above the exit hopper 44 therebelow. In this manner it facilitates placement of fertile eggs 16 from the transfer head 36 into the egg receiving buffer recesses 48 of the buffer container 46 therebelow. The buffer container 46 is operatively connected to the controller 30 to control movement thereof between the buffer rest position 50 and the buffer receiving position 52.

A buffer camera 54 may also be included within the third station 3 above the buffer rest position 50 of the buffer container 46 such that it is directed downwardly to provide photographic and recorded images of the positions of fertile eggs 16 located within the egg receiving buffer recesses 48 of container tray 46. This buffer camera 54 will be preferably operatively connected to the controller to provide recorded images thereto for noting the positions of fertile eggs 16 therewithin.

A fourth station 4 may be included within the apparatus of the present invention positioned longitudinally along the main conveyor 20 adjacent the outfeed station 24 and laterally adjacent the third station 3. This fourth station 4 will be adapted to receive trays 12 moving along the main conveyor 20 from the first station 1.

A pick and place device 56 is also included in the apparatus of the present invention to facilitate the movement of fertile eggs 16 to the trays 12 at fourth station 4. This pick and place device 56 preferably is positioned adjacent the third station 3 and the fourth station 4 and is operatively secured to the controller 30 for controlling operation thereof. The controller 30 is operative responsive to any of the egg receiving trays recesses 14 being empty as indicated on the recorded photographic image of the candling camera 34 to urge the pick and place device 56 to move to the third station 3 above the buffer container 46 to selectively remove a fertile egg 16 for placement into an open tray space. The configuration of the pick and place device 56 preferably includes a head 58 which is vertically movable as well as a lateral bar 60 which allows lateral movement perpendicular to the direction of movement of the conveyor 20 and longitudinal rails 62 which allow longitudinal movement of the head 58 with respect to the conveyor 20. In this manner all vertical, lateral and longitudinal degrees of three dimensional movement will be provided and the pickup head 58 can be moved to any chosen location to remove a fertile egg 16 from the buffer container 46 for movement therein to one of the empty egg receiving tray recesses 14 in trays 12 located in the fourth station 4.

Under certain circumstances of operation of the present invention an empty tray will be moved from the first station 1 to the fourth station 4 by the main conveyor 20. To prevent movement of this empty tray outwardly through the outfeed station 24 a verification camera 66 is preferably positioned above the fourth station 4. Verification camera 66 determines whether a tray 12 is completely empty and contains no eggs whatsoever. If an empty tray is sensed at fourth station 4 then an empty tray removal apparatus 64 will be movable to the fourth station 4 for removal of that tray to prevent it from passing outwardly through the outfeed station 24.

In operation the apparatus of the present invention will initially need to move fertile eggs 16 into the buffer container 46. This initial loading or charging of the buffer container 46 will automatically occur whenever the buffer camera 54 senses that there are no eggs located within the buffer container 46. This will be the status at the time of initiation of operation of this apparatus during a given work cycle or at the beginning of a work day.

The first tray 12 of eggs 10 will be placed at the infeed station 22. Conveyor 26 will move the tray of eggs into the first station 1. The candling camera 34 will form a digital video image of the eggs and will transmit that image to the controller 30 for analysis. The controller 30 will earmark which eggs at which positions in the 6×7 array are infertile. At this point the transfer head 36 will be caused to move to the first transfer head position 38 and vacuum will be applied to the vacuum gripping cups 42 and all eggs from within the tray 12 will be moved by the transfer head 36 to second station 2.

Once all eggs have been moved to second station 2 the earmarked infertile eggs will be released and will pass downwardly into the exit hopper 44 therebelow. At this point the buffer container 46 will move from the buffer rest position 50 in third station 3 to the buffer receiving position 52 in the second station 2 immediately below the transfer head 36. Transfer head 36 will then release the remaining eggs which are all fertile into the egg receiving buffer recesses 48 of buffer container 46. Buffer container 46 will then be moved by operation of the controller 30 to the buffer rest position 50 within third station 3.

Simultaneously therewith the now empty egg tray 12 will be conveyed by the main conveyor 20 to the fourth station 4. At this location the verification camera 66 will sense that an empty tray has entered fourth station 4 and the empty removal member device 64 will be activated and will move to a position immediately above the empty container 12 for grabbing and removal thereof.

Simultaneously with this removal a new tray of mostly fertile eggs will be introduced into the infeed station 22 and will be conveyed to the first station 1 by the main conveyor 20. The candling camera 34 will be activated and, as such, render a digital video image of this next tray which will be transmitted to the control means 30. The control means will note which of the eggs in the 6×7 forty-two egg array are infertile. If there is at least one infertile egg the transfer head 36 will then be moved to the first transfer head position 38 below the candling camera 34 and above the egg tray 12. The controller 30 will then apply vacuum to those vacuum gripping cups 42 which are located at addresses on the array where an infertile egg 18 is located. As such, the infertile eggs 18 will be lifted by the transfer head 36 as it starts on its return path of movement to the second transfer head position 40. Once it reaches this position all of the grabbed infertile eggs 18 will be released to move downwardly into the exit hopper 44. The tray 12 will simultaneously be conveyed by the main conveyor 20 to fourth station 4. Once the tray reaches the fourth station 4 the conveyor 20 will stop.

The controller 30 will have earmarked those addresses in the array of the egg tray 12 which do not have an egg. That is, the controller will know which of the specific egg receiving tray recesses 14 are empty. As long as there is at least one such empty recess the pick and place device 56 will be activated to move to the third station 3 where it will pick up at least one fertile egg and transfer it to fourth station 4 for placement into the specifically empty egg receiving tray recesses 14. This movement cycle of the pick and place device 56 will be repeated until all egg receiving tray recesses 14 contain fertile eggs 16. At this point the main conveyor 20 will be activated to cause the egg tray 12 to move to the outfeed station 24. In this manner a completely filled tray of all fertile eggs 16 can be provided for processing such as vaccination.

This process is repeated for each tray of eggs until the supply of fertile eggs within the buffer container 46 is depleted. Once that is depleted, the initial step of charging or reloading of eggs 10 into the buffer container 46 is achieved responsive to the buffer camera 54 generating a signal to the controller 30 that indicates the buffer container 46 needs to be re-supplied with fertile eggs.

It should be appreciated that the apparatus of the present invention is usable with any array of eggs from a single egg to much larger arrays than merely forty-two. The number of rows and columns can vary widely. However, for the purposes of this embodiment, a 6×7 array of forty-two eggs was utilized.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. An apparatus for candling eggs and for filling trays having an array of egg receiving tray recesses therein with fertile eggs comprising:

A. a main conveying means for moving trays, said main conveying means defining an infeed station means and an outfeed station means longitudinally spatially disposed from one another, said infeed station means operative to receive trays of eggs for candling thereof, said outfeed station means operative to provide trays filled with fertile eggs for movement outwardly therefrom, said main conveying means being operable to selectively move trays longitudinally from said infeed station means toward said outfeed station means;

B. a control means operatively connected to said main conveying means to selectively control operation thereof and the movement of trays therealong from said infeed station means to said outfeed station means;

C. a first station means positioned adjacent said main conveying means for candling trays of eggs transferred thereon from said infeed station means responsive to operation of said main conveying means, said first station means including:

(1) a primary lighting means positioned below said main conveying means within said first station means and adapted to transmit light upwardly therefrom through each egg located upon a tray on said main conveying means within said first station means to facilitate candling of eggs therein;

(2) a candling camera means positioned above said main conveying means and directed downwardly to provide photographically recorded images of a tray of eggs traveling within said first station means on said main conveying means therebelow for candling thereof, said candling camera means being operatively connected to said control means to communicate photographically recorded images thereto for analysis thereof;

D. a second station means located laterally adjacent said first station means and including:

(1) a transfer head means movably mounted within said second station means, said transfer head means being movable between a first transfer head position within said first station means and a second transfer head position within said second station means, said transfer head means including a plurality of egg gripping means extendable downwardly therefrom and adapted to grasp an egg therebelow while located within said first transfer head position to facilitate lifting and removal of eggs selectively from trays located within said first station means for movement thereof along with said transfer head means from said first transfer head position to said second transfer head position, said transfer head means being operatively connected to said control means to control movement thereof between said first transfer head position and said second transfer head position and gripping of eggs by said egg gripping means;

(2) an exit hopper means positioned below said second transfer head position within said second station means, said exit hopper means adapted to receive and accumulate infertile eggs released from said egg gripping means of said transfer head means while in said second transfer head position within said second station means;

E. a third station means positioned longitudinally adjacent said second station means and adjacent said main conveying means, said third station means including:

(1) a buffer container means movably positioned therein, said buffer container means defining a plurality of egg receiving buffer recesses therein for holding of fertile eggs therewithin to facilitate placement thereof into trays upon said main conveying means prior to movement thereof to said outfeed station means, said buffer container means being movable between a buffer rest position within said third station means ready to supply fertile eggs therefrom and a buffer receiving position within said second station means, said buffer receiving position being located within said second station means below said first transfer head position of said transfer head means and above said exit hopper means therebelow to facilitate placement of fertile eggs from said transfer head means into said egg receiving buffer recesses of said buffer container means therebelow, said buffer container means being operatively connected to said control means to control movement thereof between said buffer rest position and said buffer receiving position;

(2) a buffer camera means located above said buffer rest position of said buffer container means and directed downwardly to provide photographically recorded images of the positions of fertile eggs located within said buffer container means therebelow, said buffer camera means operatively connected to said control means to provide recorded images thereto of positions of fertile eggs within said buffer container means;

F. a fourth station means positioned longitudinally along said main conveying means adjacent said outfeed station means and laterally adjacent said third station means, said fourth station means adapted to receive trays moved by said main conveying means from said first station means thereto; and G. a pick and place device positioned adjacent said third station means and said fourth station means and being operatively secured to said control means for controlling operation thereof, said control means operative responsive to any of the egg receiving tray recesses being empty as indicated by analysis of the recorded photographic image from said candling camera means to urge said pick and place device to move to said third station means above said buffer container means to selectively remove at least one fertile egg therefrom and to thereafter move to said fourth station means above a tray on said main conveying means therein in order to place a fertile egg into any empty egg receiving tray recess therein.

2. An apparatus for candling eggs and filling trays having an array of egg receiving tray recesses therein with fertile eggs as defined in claim 1 wherein said first transfer head position of said first transfer head is located within said first station means below said candling camera means therein and above said main conveying means and a tray of eggs being transferred thereon.

3. An apparatus for candling eggs and filling trays having an array of egg receiving tray recesses therein with fertile eggs as defined in claim 1 wherein said fourth station means is positioned longitudinally along said main conveying means downstream of said first station means.

4. An apparatus for candling eggs and filling trays having an array of egg receiving tray recesses therein with fertile eggs as defined in claim 1 further comprising an empty tray removal means positioned adjacent said fourth station means and operative to remove a tray which is empty from said fourth station means prior to movement thereof to said outfeed station means.

5. An apparatus for candling eggs and filling trays having an array of egg receiving tray recesses therein with fertile eggs as defined in claim 4 wherein said fourth station means includes a verification camera means positioned above said main conveying means and being directed downwardly to be operative to determine whenever a tray positioned upon said main conveying means within said fourth station means is empty in order to initiate operation of said empty tray removal means to prevent a tray which is empty from moving to said outfeed station means.

6. An apparatus for candling eggs and filling trays having an array of egg receiving tray recesses therein with fertile eggs as defined in claim 1 wherein trays and said main conveying means are at least partially translucent to allow light from said primary lighting means to pass therethrough to eggs positioned within said egg receiving tray recesses in said first station means.

7. An apparatus for candling eggs and filling trays having an array of egg receiving tray recesses therein with fertile eggs as defined in claim 1 wherein said egg gripping means comprise vacuum gripping cups which are operative to grip eggs by the applying of a vacuum thereinto.

8. An apparatus for candling eggs and filling trays having an array of egg receiving tray recesses therein with fertile eggs as defined in claim 1 wherein said transfer head means is operable responsive to said control means determining the presence of at least one infertile egg located within a tray in said first station means to move to said first transfer head position above the tray and actuate said egg gripping means in abutment with any infertile egg and to remove any infertile egg from the tray for movement to said second transfer head position for release into said exit hopper means therebelow.

9. An apparatus for candling eggs and filling trays having an array of egg receiving tray recesses therein with fertile eggs as defined in claim 1 wherein said transfer head means is operable responsive to said control means determining that said buffer container means is empty of fertile eggs to move to said first transfer head position above the tray and to actuate said egg gripping means in abutment with all eggs located within the tray therebelow and to carry the eggs to said second transfer head position within said second station means, said control means being responsive to cause deactivation of any of those of said egg gripping means holding an infertile egg therein for movement into said exit hopper means therebelow.

10. An apparatus for candling eggs and filling trays having an array of egg receiving tray recesses therein with fertile eggs as defined in claim 9 wherein said buffer tray means is operable responsive to said control means determining that said buffer tray means is empty of fertile eggs to move to said buffer receiving position within said second station means below said transfer head means and responsive to said control means deactivating said egg gripping means thereof to allow placement of fertile eggs therefrom into the egg receiving buffer recesses thereof for reloading of said buffer tray means with fertile eggs.

11. An apparatus for candling eggs and filling trays having an array of egg receiving tray recesses therein with fertile eggs as defined in claim 10 wherein said control means is operative responsive to said buffer container means being reloaded with fertile eggs to move same to said buffer rest position within said third station means to supply fertile eggs to said pick and place device to facilitate placement of fertile eggs into empty egg receiving tray recesses within trays located in said fourth station means.

12. An apparatus for candling eggs and filling trays having an array of egg receiving tray recesses therein with fertile eggs as defined in claim 1 wherein said pick and place device has three dimensional controlled movement vertically, laterally and longitudinally to facilitate movement of fertile eggs from said egg receiving buffer recesses within said third station means into said egg receiving tray recesses of trays located in said fourth station means.

13. An apparatus for candling eggs and filling trays having an array of egg receiving tray recesses therein with fertile eggs as defined in claim 1 wherein said candling camera means comprises a digital video camera.

14. An apparatus for candling eggs and filling trays having an array of egg receiving tray recesses therein with fertile eggs as defined in claim 13 wherein said control means includes a video frame grabber for facilitating evaluation of images recorded digitally by said digital video camera to facilitate candling.

15. An apparatus for candling eggs and filling trays having an array of egg receiving tray recesses therein with fertile eggs as defined in claim 1 wherein said first station means includes a camera housing means positioned extending around said candling camera means to enhance images recorded therewith to facilitate candling.

16. An apparatus for candling eggs and filling trays having an array of egg receiving tray recesses therein with fertile eggs as defined in claim 1 wherein said primary lighting means includes a plurality of individual lighting modules therein operatively connected to said control means to facilitate control of lighting therewith.

17. An apparatus for candling eggs and filling trays having an array of egg receiving tray recesses therein with fertile eggs as defined in claim 1 wherein said control means indicates an infertile egg responsive to an egg within a tray in said first station means whenever an egg has a translucence greater than a predetermined threshold value resulting in movement thereof by said transfer head means to said exit hopper means.

18. An apparatus for candling eggs and filling trays having an array of egg receiving tray recesses therein with fertile eggs as defined in claim 1 wherein said exit hopper means comprises a disposal receptacle.

19. An apparatus for candling eggs and for filling trays having an array of egg receiving tray recesses therein with fertile eggs comprising:

A. a main conveying means for moving trays, said main conveying means defining an infeed station means and an outfeed station means longitudinally spatially disposed from one another, said infeed station means operative to receive trays of eggs for candling thereof, said outfeed station means operative to provide trays filled with fertile eggs for movement outwardly therefrom, said main conveying means being operable to selectively move trays longitudinally from said infeed station means toward said outfeed station means;

B. a control means operatively connected to said main conveying means to selectively control operation thereof and the movement of trays therealong from said infeed station means to said outfeed station means;

C. a first station means positioned adjacent said main conveying means for candling of eggs in trays transferred thereon from said infeed station means responsive to operation of said main conveying means, said first station means including:
  (1) a primary lighting means positioned below said main conveying means within said first station means and adapted to transmit light upwardly therefrom through each egg located upon a tray on said main conveying means within said first station means to facilitate candling of eggs therein;
  (2) a candling camera means comprising a digital video camera positioned above said main conveying means and directed downwardly to provide photographically recorded images of trays of eggs traveling within said first station means on said main conveying means therebelow for candling thereof, said candling camera means being operatively connected to said control means to communicate photographically recorded images thereto for analysis thereof;
  (3) a camera housing means positioned extending around said candling camera means to enhance images recorded therewith to facilitate candling of egg therebelow;

D. a second station means located laterally adjacent said first station means and including:
  (1) a transfer head means movably mounted within said second station means, said transfer head means being movable between a first transfer head position within said first station means and a second transfer head position within said second station means, said transfer head means including a plurality of egg gripping means extendable downwardly therefrom and adapted to grasp an egg therebelow while located within said first transfer head position to facilitate lifting and removal of eggs selectively from trays located within said first station means for movement thereof along with said transfer head means from said first transfer head position to said second transfer head position, said egg gripping means comprising vacuum gripping cups which are operative to grip eggs by the applying of a vacuum thereinto, said transfer head means being operatively connected to said control means to control movement thereof between said first transfer head position and said second transfer head position and gripping of eggs by said egg gripping means, said first transfer head position of said first transfer head being located within said first station means below said candling camera means therein and above said main conveying means and a tray of eggs being transferred thereon;
  (2) an exit hopper means positioned below said second transfer head position within said second station means, said exit hopper means adapted to receive and accumulate infertile eggs released from said egg gripping means of said transfer head means while in said second transfer head position within said second station means, said transfer head means being operable responsive to said control means determining the presence of at least one infertile egg located within an tray in said first station means to move to said first transfer head position above the tray and actuate said egg gripping means in abutment with any infertile egg and to remove any infertile egg from the tray for movement to said second transfer head position for release into said exit hopper means therebelow;

E. a third station means positioned longitudinally adjacent said second station means and adjacent said main conveying means, said third station means including:
  (1) a buffer container means movably positioned therein, said buffer container means defining a plurality of egg receiving buffer recesses therein for holding of fertile eggs therewithin to facilitate placement thereof into trays upon said main conveying means prior to movement thereof to said outfeed station means, said buffer container means being movable between a buffer rest position within said third station means ready to supply fertile eggs therefrom and a buffer receiving position within said second station means, said buffer receiving position being located within said second station means below said first transfer head position of said transfer head means and above said exit hopper means therebelow to facilitate placement of fertile eggs from said transfer head means into said egg receiving buffer recesses of said buffer container means therebelow, said buffer container means being operatively connected to said control means to control movement thereof between said buffer rest position and said buffer receiving position;
  (2) a buffer camera means located above said buffer rest position of said buffer container means and directed downwardly to provide photographically recorded images of the positions of fertile eggs located within said buffer container means therebelow, said buffer camera means operatively connected to said control means to provide recorded images thereto of positions of fertile eggs within said buffer container means;

F. a fourth station means positioned longitudinally along said main conveying means adjacent said outfeed station means and laterally adjacent said third station means, said fourth station means adapted to receive trays moved by said main conveying means from said first station means thereto;

G. an empty tray removal means positioned adjacent said fourth station means and operative to remove trays which are empty therefrom prior to movement thereof to said outfeed station means;

H. a verification camera means positioned above said main conveying means and being directed downwardly to be operative to determine whenever an tray positioned upon said main conveying means within said fourth station means is empty in order to initiate operation of said empty tray removal means to prevent an tray empty of eggs from moving to said outfeed station means; and I. a pick and place device positioned adjacent said third station means and said fourth station means and being operatively secured to said control means for controlling operation thereof, said control means operative responsive to any of the egg receiving tray recesses being empty as indicated by analysis of the recorded photographic image from said candling camera means to urge said pick and place device to move to said third station means above said buffer container means to selectively remove at least one fertile egg therefrom and to thereafter move to said fourth station means above an tray on said main conveying means therein in order to place a fertile egg into any empty egg receiving tray recess therein.

20. An apparatus for candling eggs and for filling trays having an array of egg receiving tray recesses therein with fertile eggs comprising:

A. a main conveying means for moving trays, said main conveying means defining an infeed station means and an outfeed station means longitudinally spatially disposed from one another, said infeed station means operative to receive trays of eggs for candling thereof, said outfeed station means operative to provide trays filled with fertile eggs for movement outwardly therefrom, said main conveying means being operable to selectively move trays longitudinally from said infeed station means toward said outfeed station means;

B. a control means operatively connected to said main conveying means to selectively control operation thereof and the movement of trays therealong from said infeed station means to said outfeed station means, said control means including a video frame grabber to facilitate candling;

C. a first station means positioned adjacent said main conveying means for candling trays of eggs transferred thereon from said infeed station means responsive to operation of said main conveying means, said first station means including:

(1) a primary lighting means positioned below said main conveying means within said first station means and adapted to transmit light upwardly therefrom through each egg located upon a tray on said main conveying means within said first station means to facilitate candling of eggs therein, each tray and said main conveying means being at least partially translucent to allow light from said primary lighting means to pass therethrough to eggs positioned within said egg receiving tray recesses in said first station means, said primary lighting means including a plurality of individual lighting modules therein operatively connected to said control means to facilitate control of lighting therewith;

(2) a candling camera means comprising a digital video camera positioned above said main conveying means and directed downwardly to provide photographically recorded images of trays of eggs traveling within said first station means on said main conveying means therebelow for candling thereof, said candling camera means being operatively connected to said control means to communicate photographically recorded images thereto for analysis thereof;

(3) a camera housing means positioned extending around said candling camera means to enhance images recorded therewith to facilitate candling of egg therebelow;

D. a second station means located laterally adjacent said first station means and including:

(1) a transfer head means movably mounted within said second station means, said transfer head means being movable between a first transfer head position within said first station means and a second transfer head position within said second station means, said transfer head means including a plurality of egg gripping means extendable downwardly therefrom and adapted to grasp an egg therebelow while located within said first transfer head position to facilitate lifting and removal of eggs selectively from trays located within said first station means for movement thereof along with said transfer head means from said first transfer head position to said second transfer head position, said egg gripping means comprising vacuum gripping cups which are operative to grip eggs by the applying of a vacuum thereinto, said transfer head means being operatively connected to said control means to control movement thereof between said first transfer head position and said second transfer head position and gripping of eggs by said egg gripping means, said first transfer head position of said first transfer head being located within said first station means below said candling camera means therein and above said main conveying means and a tray of eggs being transferred thereon;

(2) an exit hopper means positioned below said second transfer head position within said second station means, said exit hopper means adapted to receive and accumulate infertile eggs released from said egg gripping means of said transfer head means while in said second transfer head position within said second station means, said transfer head means being operable responsive to said control means determining the presence of at least one infertile egg located within a tray in said first station means to move to said first transfer head position above the tray and actuate said egg gripping means in abutment with any infertile egg and to remove same from the tray for movement to said second transfer head position for release into said exit hopper means therebelow, said control means being operative to indicate an infertile egg responsive to an egg within an tray in said first station means whenever an egg has a translucence greater than a predetermined threshold value resulting in movement thereof by said transfer head means to said exit hopper means, said exit hopper means comprising a disposal receptacle;

E. a third station means positioned longitudinally adjacent said second station means and adjacent said main conveying means, said third station means including:

(1) a buffer container means movably positioned therein, said buffer container means defining a plurality of egg receiving buffer recesses therein for holding of fertile eggs therewithin to facilitate placement thereof into trays upon said main conveying means prior to movement thereof to said outfeed station means, said buffer container means being movable between a buffer rest position within said third station means ready to supply fertile eggs therefrom and a buffer receiving position within said second station means, said buffer receiving position being located within said second station means below said first transfer head position of said transfer head means and above said exit hopper means therebelow to facilitate placement of fertile eggs from said transfer head means into said egg receiving buffer recesses of said buffer container means therebelow, said buffer container means being operatively connected to said control means to control movement thereof between said buffer rest position and said buffer receiving position, said transfer head means being operable responsive to said control means determining that said buffer container means is empty of fertile eggs to move to said first transfer head position above the tray and to actuate said egg gripping means in abutment with all eggs located within the tray therebelow and to carry same to said second transfer head position within said second station means, said control means being responsive to cause deactivation of any of those of said egg gripping means holding an infertile egg therein for movement into said exit hopper means therebelow, said buffer container means being operable responsive to said control means determining that said buffer container means is empty of fertile eggs to move to said buffer receiving position within said second station means below said transfer head means and responsive to said control means deactivating said egg gripping means thereof to allow placement of fertile eggs therefrom into the egg receiving buffer recesses thereof for reloading of said buffer container means with fertile eggs, said control means being operative responsive to said buffer container means being reloaded with fertile eggs to move same to said buffer rest position within said third station means to supply fertile eggs for facilitating placement of fertile eggs into empty egg receiving tray recesses within trays located in said fourth station means;

(2) a buffer camera means located above said buffer rest position of said buffer container means and directed downwardly to provide photographically recorded images of the positions of fertile eggs located within said buffer container means therebelow, said buffer camera means operatively connected to said control means to provide recorded images thereto of positions of fertile eggs within said buffer container means;

F. a fourth station means positioned longitudinally along said main conveying means downstream of said first station means adjacent said outfeed station means and laterally adjacent said third station means, said fourth station means adapted to receive egg trays moved by said main conveying means from said first station means thereto;

G. an empty tray removal means positioned adjacent said fourth station means and operative to remove a tray empty of eggs therefrom prior to movement thereof to said outfeed station means;

H. a verification camera means positioned above said main conveying means and being directed downwardly to be operative to determine whenever an tray positioned upon said main conveying means within said fourth station means is empty in order to initiate operation of said empty tray removal means to prevent a tray which is empty from moving to said outfeed station means; and I. a pick and place device positioned adjacent said third station means and said fourth station means and being operatively secured to said control means for controlling operation thereof, said control means operative responsive to any of the egg receiving tray recesses being empty as indicated by analysis of the recorded photographic image from said candling camera means to urge said pick and place device to move to said third station means above said buffer container means to selectively remove at least one fertile egg therefrom and to thereafter move to said fourth station means above an tray on said main conveying means therein in order to place a fertile egg into any empty egg receiving tray recess therein, said pick and place device having three dimensional controlled movement vertically, laterally and longitudinally to facilitate movement of fertile eggs from said egg receiving buffer recesses within said third station means into said egg receiving tray recesses of trays located in said fourth station means.

21. A method for candling eggs and for filling trays having an array of egg receiving tray recesses therein with fertile eggs which comprises:

A. initial loading of a buffer container located at a third station with fertile eggs;

B. providing a tray of eggs at an input station with a plurality of egg receiving tray recesses defined therewithin;

C. first conveying of a tray of eggs from the input station to a first station;

D. candling of eggs located in the egg receiving recesses of a tray in the first station to identify which eggs therein are fertile and which eggs therein are infertile;

E. moving of a transfer head laterally from a second station into the first station;

F. gripping by the transfer head of only the infertile eggs identified by said candling of eggs in the first station;

G. transferring of the gripped infertile eggs by the transfer head from the first station to the second station for accumulation thereof within an exit hopper;

H. second conveying of a tray containing fertile eggs from the first station to a fourth station;

I. transporting fertile eggs from a buffer container within the third station to fill any empty egg receiving tray recesses within an tray at the fourth station; and J. third conveying of a tray filled with fertile eggs from the fourth station to the outfeed station.

22. A method for candling eggs and for filling trays having an array of egg receiving tray recesses therein with fertile eggs as defined in claim 21 wherein said initial loading of a buffer tray located at a third station with fertile eggs comprises:

A. preliminary placing of a tray of eggs at the input station;

B. preliminary conveying of a tray of eggs to the first station from the input station;

C. preliminary candling of the tray within the first station to identify which eggs therein are fertile and which eggs therein are infertile;

D. preliminary moving of a transfer head from the second station to the first station;

E. preliminary gripping by the transfer head of all eggs from a tray therebelow;

F. preliminary relocating of the transfer head with eggs retained thereto from a first station to a second station;

G. preliminary releasing by the transfer head of any infertile eggs into an exit hopper therebelow;

H. relocating of a buffer tray from a third station to a second station at a position below the transfer head;

I. loading of fertile eggs into the egg receiving buffer recesses of the buffer tray therebelow by releasing of eggs retained by the transfer head; and J. returning of the buffer tray from a second station to a third station.

23. A method for candling eggs and for filling trays having an array of egg receiving tray recesses therein with fertile eggs as defined in claim 21 wherein said candling of eggs located in the egg receiving recesses of a tray comprises:

A. passing light through eggs located in the egg receiving tray recesses within the first station; and B. digitally photographing a pattern of light passing through the eggs within the first station.

24. A method for candling eggs and for filling trays having an array of egg receiving tray recesses therein with fertile eggs as defined in claim 23 wherein said digital photographing comprises digitally video taping of light passing upwardly through eggs located in the egg receiving recesses of trays in the first station for determining the fertility thereof.

25. A method for candling eggs and for filling trays having an array of egg receiving tray recesses therein with fertile eggs as defined in claim 23 wherein said candling of eggs located in the egg receiving recesses of a tray further includes digitally scanning photographs of the light pattern passing through eggs within the first station to determine the fertility thereof.

26. A method for candling eggs and for filling trays having an array of egg receiving tray recesses therein with fertile eggs as defined in claim 21 further comprising discarding infertile eggs accumulated within exit hopper.

27. A method for candling eggs and for filling trays having an array of egg receiving tray recesses therein with fertile eggs as defined in claim 21 further comprising providing of a light shield housing positioned adjacent the first station to facilitate candling therewithin.

28. A method for candling eggs and for filling trays having an array of egg receiving tray recesses therein with fertile eggs as defined in claim 21 further comprising final monitoring of trays at the third station to indicate if any tray at the third station is empty.

29. A method for candling eggs and for filling trays having an array of egg receiving tray recesses therein with fertile eggs as defined in claim 28 wherein said final monitoring is performed with a verification video camera to provide continuous indication whether the buffer tray is empty.

30. A method for candling eggs and for filling trays having an array of egg receiving tray recesses therein with fertile eggs as defined in claim 28 further comprising actuating of a tray removal device responsive to said final monitoring indicating a tray which is empty is located at the third station to remove a tray which is empty from the third station.

31. A method for candling eggs and for filling trays having an array of egg receiving tray recesses therein with fertile eggs as defined in claim 21 wherein said first conveying, said second conveying and said third conveying are performed in a longitudinal direction and wherein the transfer head is movable between the second station and the first station laterally and perpendicularly with respect to the longitudinal direction.

32. A method for candling eggs and for filling trays having an array of egg receiving tray recesses therein with fertile eggs as defined in claim 21 further comprising buffer monitoring of the buffer tray within the third station to indicate if the buffer tray becomes empty.

33. A method for candling eggs and for filling trays having an array of egg receiving tray recesses therein with fertile eggs as defined in claim 21 further comprising final conveying of a tray of fertile eggs from the outfeed station to a vaccination station.

34. A method for candling eggs and for filling trays having an array of egg receiving tray recesses therein with fertile eggs as defined in claim 33 further comprising vaccinating of the trays filled with fertile eggs to make the fertile embryos developing therein resistant to disease and infection.

35. A method for candling eggs and for filling trays having an array of egg receiving tray recesses therein with fertile eggs as defined in claim 21 further comprising providing a controller device operative to monitor and control candling and movement of eggs and trays.

36. A method for candling eggs and for filling trays having an array of egg receiving tray recesses therein with fertile eggs as defined in claim 35 wherein the controller device is a computerized controlling apparatus.

37. A method for candling eggs and for filling trays having an array of egg receiving tray recesses therein with fertile eggs as defined in claim 21 wherein said gripping of eggs by the transfer head comprises placing of vacuum cup in abutment with eggs and the applying of a vacuum thereto.

38. A method for candling eggs and for filling trays having an array of egg receiving tray recesses therein with fertile eggs as defined in claim 21 wherein said transporting fertile eggs from a buffer container within the third station to filled any empty egg receiving tray recesses within the tray at the fourth station is performed by a three-dimensionally movable pick and place device movably positionable within the third station for fertile egg picking from the buffer container and within the fourth station for fertile egg placing in an tray therebelow.

39. A method for candling eggs and for filling trays having an array of egg receiving tray recesses therein with fertile eggs which comprises:

A. preliminary placing of a tray of eggs at the input station;

B. preliminary conveying of a tray of eggs to the first station from the input station;

C. preliminary candling of the tray within the first station to identify which eggs therein are fertile and which eggs therein are infertile;

D. preliminary moving of a transfer head from the second station to the first station;

E. preliminary gripping by the transfer head of all eggs from a tray therebelow;

F. preliminary relocating of the transfer head with eggs retained thereto from a first station to a second station;

G. preliminary releasing by the transfer head of any infertile eggs into an exit hopper therebelow;

H. relocating of a buffer container from a third station to a second station at a position below the transfer head;

I. loading of fertile eggs into the egg receiving buffer recesses of the buffer container therebelow by releasing of eggs retained by the transfer head;

J. returning of the buffer container from a second station to a third station;

K. providing a tray of eggs at an input station with a plurality of egg receiving tray recesses defined therewithin;

L. first conveying of a tray of eggs from the input station to a first station;

M. candling of eggs located in the egg receiving recesses of a tray in the first station to identify which eggs therein are fertile and which eggs therein are infertile, said candling including passing light through eggs located in the egg receiving tray recesses within the first station and digitally photographing by video taping of a pattern of light passing through the eggs within the first station, said candling of eggs further including digitally scanning photographs of the light pattern passing through eggs within the first station to determine fertility thereof;

N. moving of a transfer head laterally from a second station into the first station;

O. gripping by the transfer head of only the infertile eggs identified by said candling of eggs in the first station said gripping of eggs by the transfer head by placing of vacuum cup in abutment with infertile eggs and the applying of a vacuum thereto;

P. transferring of the gripped infertile eggs by the transfer head from the first station to the second station for accumulation thereof within an exit hopper;

Q. second conveying of a tray containing fertile eggs from the first station to a fourth station;

R. final monitoring of trays at the third station by a verification video camera to indicate if any tray at the third station is empty;

S. actuating of a tray removal device responsive to said final monitoring indicating a tray which is empty at the third station to remove a tray which is empty therefrom;

T. transporting fertile eggs from a buffer container within the third station to fill any empty egg receiving tray recesses within an tray at the fourth station;

U. third conveying of a tray filled with fertile eggs from the fourth station to the outfeed station;

V. buffer monitoring of the buffer container within the third station to indicate if the buffer container becomes empty;

W. moving to the step of preliminary placing if the buffer container is empty; and X. moving to the step of providing a tray of eggs at an input station with a plurality of egg receiving tray recesses defined therewithin if the buffer container is not empty.

40. A method for candling eggs and for filling trays having an array of egg receiving tray recesses therein with fertile eggs which comprises:

A. preliminary placing of a tray of eggs at the input station;

B. preliminary conveying of a tray of eggs to the first station from the input station;

C. preliminary candling of the tray within the first station to identify which eggs therein are fertile and which eggs therein are infertile;

D. preliminary moving of a transfer head from the second station to the first station;

E. preliminary gripping by the transfer head of all eggs from a tray therebelow;

F. preliminary relocating of the transfer head with eggs retained thereto from a first station to a second station;

G. preliminary releasing by the transfer head of any infertile eggs into an exit hopper therebelow;

H. relocating of a buffer container from a third station to a second station at a position below the transfer head;

I. loading of fertile eggs into the egg receiving buffer recesses of the buffer container therebelow by releasing of eggs retained by the transfer head;

J. returning of the buffer container from a second station to a third station;

K. providing a tray of eggs at an input station with a plurality of egg receiving tray recesses defined therewithin;

L. first conveying in a longitudinal direction of a tray of eggs from the input station to a first station;

M. candling of eggs located in the egg receiving recesses of a tray in the first station to identify which eggs therein are fertile and which eggs therein are infertile, said candling including passing light through eggs located in the egg receiving tray recesses within the first station and digitally photographing by video taping of a pattern of light passing through the eggs within the first station, said candling of eggs further including digitally scanning photographs of the light pattern passing through eggs within the first station to determine fertility thereof;

N. moving of a transfer head laterally from a second station into the first station;

O. gripping by the transfer head of only the infertile eggs identified by said candling of eggs in the first station;

P. transferring of the gripped infertile eggs by the transfer head from the first station to the second station for accumulation thereof within an exit hopper for disposal;

Q. second conveying in a longitudinal direction of a tray containing fertile eggs from the first station to a fourth station;

R. final monitoring of trays at the third station by a verification video camera to indicate if any tray at the third station is empty;

S. actuating of a tray removal device responsive to said final monitoring indicating a tray which is empty at the third station to remove a tray which is empty therefrom;

T. transporting fertile eggs from a buffer container within the third station to fill any empty egg receiving tray recesses within an tray at the fourth station by providing a three-dimensionally movable pick and place device movably positionable within the third station for fertile egg picking from the buffer container and within the fourth station for fertile egg placing in an tray therebelow;

U. third conveying in a longitudinal direction of a tray filled with fertile eggs from the fourth station to the outfeed station;

V. buffer monitoring of the buffer container within the third station to indicate if the buffer container becomes empty;

W. moving to the step of preliminary placing if the buffer container is empty;

X. moving to the step of providing a tray of eggs at an input station with a plurality of egg receiving tray recesses defined therewithin if the buffer container is not empty;

Y. final conveying in a longitudinal direction of a tray of fertile eggs from the outfeed station to a vaccination station; and Z. vaccinating of trays filled with fertile eggs to enhance resistance to disease and infection of the fertile embryos developing therein.

* * * * *